US006656907B1

(12) United States Patent
Buret et al.

(10) Patent No.: US 6,656,907 B1
(45) Date of Patent: *Dec. 2, 2003

(54) METHOD OF TREATING GASTRIC ULCER BY ADMINISTRATION OF EPIDERMAL GROWTH FACTOR

(75) Inventors: Andre G. Buret, Calgary (CA); D. Grant Gall, Calgary (CA); James A. Hardin, Calgary (CA); Merle E. Olson, Calgary (CA)

(73) Assignee: University Technologies International Inc., Alberta (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/518,135

(22) Filed: Mar. 3, 2000

Related U.S. Application Data

(63) Continuation of application No. 08/945,760, filed as application No. PCT/CA96/00291 on May 9, 1996, now abandoned, which is a continuation-in-part of application No. 08/438,901, filed on May 10, 1995, now Pat. No. 5,753,622.

(51) Int. Cl.$^7$ ...................... A61K 38/18; C07K 14/485; C07K 2/00
(52) U.S. Cl. ........................... 514/12; 514/2; 424/85.1; 424/198.1; 530/300; 530/350; 530/399
(58) Field of Search .............. 424/198.1, 85.1; 514/2, 12; 530/300, 350, 399, 351

(56) References Cited

U.S. PATENT DOCUMENTS

| 4,820,690 | A | * | 4/1989 | Gregory et al. ................ 514/12 |
| 5,578,302 | A | | 11/1996 | Brassart et al. .......... 424/93.45 |
| 5,753,622 | A | * | 5/1998 | Buret et al. .................... 514/12 |

FOREIGN PATENT DOCUMENTS

| EP | 161817 | 11/1985 |
| EP | 577903 A | 6/1992 |
| GB | 2198351 | 6/1988 |

OTHER PUBLICATIONS

Labenz et al. Evidence for the essential role of *Helicobacter pylori* in gastric ulcer disease. Gut 35: 19–22, 1994.*
Aldridge et al., Compend. N. Am. ed. 14:265–269 (1992).
Barnard et al., Gastroenterology, 108:564–580 (1996).
Bird, A.R., et al. "Jejunal Glucose Absorption is Enhanced by Epidermal Growth Factor in Mice" *Journal of Nutrition* 124:231–240 (1994).
Bijlsm, Infect. Immun., 37:891–894 (1982).
Bliska et al., Cell, 73:903–920 (1993).
Brake et al., Proc. Natl., Acad. Sci. USA, 81:4642–4646 (1984).
Brown et al., New Engl. J. Med., 321:76–79 (1989).
Brown, G.L. et al. (1986) "Enhancement of Epidermal Regeneration of by Biosynthetic Epidermal Growth Factor" *J. Exp. Med* 163: 1319–1324 (1986).

Buchmiller et al., J. Ped. Surg., 28:1239–1244 (1993).
Carpenter, Curr. Opin. Cell. Biol., 5:261–264 (1993).
Donowitz et al., Am. J. Physiol., 266: G647–G656 (1994).
Elliot et al., Gastroenterology, 106:1554–1561 (1994).
Eppstein et al., Nature, 318:663–665 (1985).
Foltzer–Jordaine et al., Am. J. Physiol., 265:6459–6466 (1993).
Galan et al., Nature, 357: 588–589 (1992)1.
Goodlad, R.A. et al. "Effects of Urogastrone–Epidermal Growth Factor on Intestinal Brush Border Enzymes and Mitotic Activity" *Gut.* 994–998 (1991).
Grimes et al., Am. J. Vet. Res., 47:385–388 (1986).
Hadad et al., Am. J. Vet. Res., 43:41–49 (1982).
Hardin, J.A. et al., "Effect of Epidermal Growth Factor on Enterocyte Brush–Border Surface Area" *Am. J. Physiol.* 264:G312–G318 (1993).
Hardin, J.A. et al., "The Effect of TGFα on Intestinal Solute Transport" *Reg. Pep,* 39: 169–176 (1992).
Horvath, K. et al., "Short–Term Effect of Epidermal Growth Factor on Sodium and Glucose Cotransport of Isolated Jejunal Epithelial Cells" *Biochem. Biophys. Acta. Mol. Cell. Res.* 1222:215–222 (1994).
Isberg R.R. et al., "Discrimination Between Intracellular Uptake and Surface Adhesion of Bacterial Pathogens" *Science,* 252:934–938 (1991).
Imada et al., Biological Abstracts, vol. 84, No. 12, Abstract No. 117708 (1987).
Jaeger, L.A. et al., "Effect of Orally Administered Epidermal Growth Factor on the Jejunal Mucosa of Weaned Pigs" *Am. J. Vet. Res.* 5(3):471–474 (1990).
James, P.S. et al., "Dexamathasone Selectively Increases Sodium–Dependent Alanine Transport Across Neonatal Piglet Intestine" *J. Physiol.* 393:569–582 (1987).
James, P.S. et al. "Epidermal Growth Factor Selectively Increases Maltase and Sucrase Activities in Nionatal Piglet Intestine" *J. Physiol.* 393:583–594 (1987).
Janke et al., JAVMA, 196:897–901 (1990).
Jiang, J. et al., Journal of Bacteriology, vol. 171, No. 10, 5244–5253 (Oct., 1989).
Karasov et al., Physiol. Gastrointes. Tract. $2^{nd}$ Ed., Johnson Raven Press, New York, 1489–1497 (1987).
Kitagawa, T. et al., "Regulations of Glucose Transport Activity and Expression of Glucose Transporter mRNA by Serum, Growth Factors, and Phorbol Ester in Quiescent Mouse Fibroblasts" *Biochem. Biophys. Acta.* 980:100–108 (1989).
Komoriya, A. et al, "Biologically Active Synthetic Fragments of Epidermal Growth Factor: Localization of a Major Receptor–Binding region" Proc. Natl. Acad. Sci. USA 81:1351–1355 (1984).

(List continued on next page.)

Primary Examiner—Elizabeth Kemmerer
Assistant Examiner—Bridget E. Bunner
(74) *Attorney, Agent, or Firm*—Burns, Doane, Swecker & Mathis LLP

(57) ABSTRACT

New utilities for epidermal growth factor (EGF) are described. In particular, EGF is useful in preventing gastrointestinal colonization by pathogens.

6 Claims, 1 Drawing Sheet

OTHER PUBLICATIONS

Lax, I. et al., Mol. Cell Biol., 8:1970–1978 (1988).
Lyall et al., J. of Biol. Chem., 264:1403–1409 (1989).
Mainil et al., Am. J. Vet. Res., 51:187–190 (1990).
Marti, U. et al., "Biological Effects of Epidermal Growth Factor with Emphasis on the Gastrointestinal Tract and Liver: An Update" *Hepatology* 9(1): 126–138.
Newsted et al., Toxicol. Apol. Pharmacol., 119:41–51 (1993).
O'Loughlin, E.V. et al. "Effect of Epidermal Growth Factor on Ontogeny of the Gastrointestinal Tract" *Am. J. Physiol.* 249:G674–G678 (1985).
O'Loughlin, E.V. et al. "Structural and Functional Adaptation Following JeJunal Resection in Rabbits: Effect of Epidermal Growth Factor" *Gastroenterology* 107:87–93 (1994).
Opleta–Madsen, K. "Epidermal Growth Factor Upregulates Intestinal Electrolyte and Nutrient Transport" *Am. J. Physiol.* 260:G807–G814 (1991).
Opleta–Madsen, K. "Epidermal Growth Factor and Postnatal Development of Intestinal Transport and Membrane Structure" *Pediatr. Res.* 30:342–350 (1991).
Opleta, "Effect of Epidermal Growth Factor on Growth and Postnatal Development of the Rabbit Liver", *Am. J. Physiol.*, 253:G622–G626 (1987).
Pace, J. et al., "Signal Transduction and Invasion of Epithelial Cells by *Salmonella Typhimurium*" *Cell.* 72:505–514 (1993).
Pascall, J.C. et al., "Cloning and Characterization of a Gene Encoding Pig Epidermal Growth Factor" *J. Mol. Endocrinol.* 6:63–70 (1991).
Playford, R.J. et al., "Effect of Luminal Growth Factor Preservation on Intestinal Growth" *Lancet.,* 341:843–848 (1993).
Pothier, P. et al. "Presence and Characteristics of Epidermal Growth Factor Receptors in Human Fetal Small Intestine and Colon" *FEBS Lett.* 228(1):113–117 (1988).
Riegler, M. et al., *Am. J. Physiol.* 273:G1014–1022 (1997).
Salloum, R.M. et al., "Regulation of Small Intestinal Glutamine Transport by Epidermal Growth Factor" *Surgery,* 113:552–559 (1993).

Schwartz, M.Z., et al., "Influence of Epidermal Growth Factor on Intestinal Function in the Rat: Comparison of Systemic Infusion Versus Luminal Perfusion" *Am. J. Surg.* 155:18–22.
Schoonderwoerd et al., *Can. J. Vet. Res.* 52:484–487 (1988).
Smith, M.W. "Postnatal Development of Transport Function in the Pig Intestine" *Comp. Biochem. Physiol.* 90A:577–582.
Strong, J.E., et al., "Evidence that Epidermal Growth Factor Receptor on Host Cells Confers Reovirus Infection Efficiency" *Virology* 197:405–411 (1993).
Tang, D. et al., "Recognition of the Epidermal Growth Factor Receptor by Reovirus" *Virology* 197:412–414 (1993).
Walker–Smith, J.A. et al., "Intravenous Epidermal Growth Factor/Urogastone Increases Small Intestinal Cell Proliferation in Congenital Microvillous Atrophy" *Lancet* ii: 1239–1240 (1985).
Weaver, L.T. et al. "Uptake and Transport of Epidermal Growth Factor by the Small Intestinal Epithelium of the Fetal Rat" *Gastroenterology* 98:828–837 (1990).
Zadunaisky et al., *J. Membrane Biol.,* 143:207–217 (1995).
Zschiesche et al., *Experientia,* 44:249–251 (1988).
Zijlstra, R.T. et al. "Effect of Orally Administered Epidermal Growth Factor in Intestinal Recovery of Neonatal Pigs Infected with Rotavirus" *J. Ped. Gastro. Nutr.* 19:382–390 (1994).
Hardin, J. et al., *Am. J. Physiol.* 271:G509–G515 (1996).
Johnson et al., *Mol. Cell. Biol.* 8(5):1970–1978 (1988).
M. Itoh, et al., "Experimental And Clinical Studies On Epidermal Growth Factor For Gastric Mucosal Protection And Healing Of Gastric Ulcers", Journal of Clinical Gastroenterology, vol. 10, No. Suppl. 1, 1998 pp. S7–S12.
S.J. Konturek, "Role Of Epidermal Growth Factor In Gastroprotection And Ulcer Healing", Scandinavian Journal of Gastroenterology, vol. 23, No. 2, 1988, pp. 129–133.
S.N. Elliott, et al., "Bacterial Colonization And Healing Of Gastric Ulcers: The Effects Of Epidermal Growth Factor", American Journal of Physiology, Gastrointestinal and Liver Physiology, vol. 278, No. 1, Jan. 2000, pp. G105–G112.

\* cited by examiner

CURVE FITS:  ——  Control:   $Y = -3.2222 + 43.1800 \, X$   $(R = 0.9985)$

- - -  EGF:   $Y = -9.2806 + 48.3117 \, X$   $(R = 0.9997)$

METHOD OF TREATING GASTRIC ULCER BY ADMINISTRATION OF EPIDERMAL GROWTH FACTOR

This application is a continuation of U.S. patent application Ser. No. 08/945,760, filed Jan. 9, 1998 (now abandoned). U.S. patent application Ser. No. 08/945,760 claims priority under 35 U.S.C. §371 to PCT/CA96/00291, internationally filed May 9, 1996, and is a continuation-in-part application of U.S. patent application Ser. No. 08/438,901, filed May 10, 1995 (now U.S. Pat. No. 5,753,622). All the above identified applications and patents are herein incorporated by reference in their entirety.

FIELD OF THE INVENTION

The present invention relates to the use of epidermal growth factor (EGF) as a gastrointestinal therapeutic agent. In particular, EGF can be used to promote weight gain and prevent gastrointestinal colonization by pathogens. EGF may also be used to increase absorption of immunoglobulins. The inhibition of the EGF signalling cascade may be used to prevent uptake of toxic or adverse compounds as well as to promote weight loss.

BACKGROUND OF THE INVENTION

A number of intestinal growth factors accelerate epithelial maturation and renewal. One of these is epidermal growth factor (EGF), a small acid stable gastrointestinal peptide that is naturally present in salivary and intestinal secretions and other body fluids, and is produced in large quantities in colostrum and milk. EGF promotes a) the proliferation and differentiation of intestinal cells during early life, b) the functional maturation of the pre-weaning intestine, and c) epithelial proliferation in the adult gut (10, 11, 12, 13, 14). Moreover, EGF acutely (within minutes) upregulates small intestinal absorption of electrolytes and nutrients, an effect which was shown to be related to a concurrent lengthening of the apical microvilli of enterocytes (15). Potential therapeutic benefits of EGF have been highlighted in studies where topical treatment with EGF promoted wound healing (30) and, more recently, by the observation that administration of EGF enhances nutrient absorption in remnant intestine following massive resection (16). Compared with the small intestine, more receptors for EGF are found in the colon (17), where the heaviest bacterial load is observed during infection with microorganisms such as *Esherichia coli*. EGF upregulates function in the entire intestine, including the colon (12, 16).

While EGF has been reported to have a variety of functions, its role in preventing intestinal colonization by pathogens or in accelerating weight gain have not been previously reported. These two newly discovered properties of EGF make it extremely useful as a therapeutic agent. The ability of EGF to prevent intestinal colonization or infection by pathogens has many important therapeutic applications. One such application is in the treatment of enteric colibacillosis in young farm animals.

Enteric colibacillosis is a bacterial infection with considerable implications for the economy of the agricultural industry. Enteric colibacillosis (also called scours) is one of the most common diseases of newborn and young farm animals (1–6). The microbe responsible for the disease is the pathogenic bacterium *Escherichia coli* (*E. coli*). The infection occurs wherever farm animals are maintained and is a significant cause of economic loss in Western Canada and other parts of the world. The disease is characterized by diarrhea, dehydration and eventual death. Therefore, there is a real need to develop a method to prevent the economic loss caused by enteric colibacillosis.

In addition to treating enteric colibacillosis in young farm animals, EGF can also be used to treat or prevent any condition that results from intestinal colonization by a pathogen, i.e. a virus (for example coronavirus, parvovirus rotavirus), a bacterium (for example Salmonella sp. and Shigella sp.) or a parasite (for example Cryptospordium sp. and Eimeria sp.) and traveller's diarrhea. Another important use of EGF is in the prevention of bacterial colonization at gastric ulcer sites. It is now well documented that infection by the bacteria *Helicobacter pylori* is a major risk factor for recurrent peptic ulcer disease. It has been shown that bacterial colonization occurs at the ulcer site and contributes to the chronicity of the ulcer. Therefore, EGF may be useful in preventing colonization of the bacteria *Helicobacter pylori* and therefore may be useful in accelerating healing of gastric ulcers.

In addition to demonstrating that administration of EGF can prevent intestinal colonization by pathogens, the inventors have also shown that EGF can enhance weight gain in animals. The latter effect is unexpected as certain publications have indicated that EGF has no effect on weight gain (21, 25). Other studies investigating the effects of EGF in pigs (28, 29) were unable to demonstrate an acceleration in growth rate, despite concurrent increases in the levels of intestinal disaccharidases.

The use of EGF in accelerating weight gain also has many important therapeutic applications. This property is useful when treating intestinal infection especially where weight loss from diarrhea and dehydration accompanies the infection. This property is also useful in increasing production in the animal industry such as in the beef, pig, poultry and fish industry. The latter industry is becoming more important as more fish are being produced through aquaculture. In the animal industry EGF can be easily administered as a food additive or in the drinking water of farm animals. The use of EGF to promote weight gain can also be used to treat malnourished people and persons suffering from anorexia nervosa.

In addition to preventing colonization by pathogens and increasing weight gain, EGF has also been shown to increase the intestinal absorption of nutrients. This property also has many therapeutic applications. For example, this property makes EGF more useful in treating intestinal infections or in promoting weight gain by increasing the absorption of nutrients that may be needed in such circumstances. Further, by upregulating gastrointestinal absorption, EGF may also increase immunoglobulin uptake in the newborn.

The major source of immunoglobulin for the newborn is maternal colostrum and milk, and failure to appropriately absorb maternal immunoglobulin correlates with high morbidity and mortality from infectious diseases (31). The rate of immunoglobulin absorption is greatest during the first days of life, after which immunoglobulin uptake decreases and gut closure occurs. Administration of EGF may (a) promote immunoglobulin absorption from colostrum, milk or other sources (such as oral immunoglobulin preparations) and (b) delay gut closure which may also enhance immunoglobulin uptake.

As discussed above, EGF causes an increase in the intestinal absorption of nutrients. Consequently, inhibition of the EGF signalling cascade reduces intestinal absorption of nutrients. The clinical benefits of inhibiting the EGF signalling cascade in the regulation of gastrointestinal nutrient absorption have never been assessed. It is predicted that antagonists of the EGF receptor or the EGF signalling cascade may be used as a gastrointestinal therapeutic agent where decreased intestinal absorption may be warranted for example in treating obesity, or to decrease intestinal uptake of toxic or adverse substances.

SUMMARY OF THE INVENTION

The present invention relates to the use of epidermal growth factor (EGF) as a gastrointestinal therapeutic agent.

In one aspect, the present invention provides the use of EGF to prevent or treat intestinal colonization by a pathogen in an animal. Intestinal infection and disease is the major cause of loss in food producing animals.

The term "animal" as used herein is meant to include all members of the animal kingdom such as fish and mammals (including farm animals and even humans).

The term "pathogen" as used herein is meant to include any organism capable of causing disease such as bacteria, viruses and parasites. Examples of bacterial pathogens that can invade the gastrointestinal system include E. coli and salmonella typhimurium.

The EGF is preferably administered orally, for example in the feed of the animal. Further, lyophilized EGF added to drinking water has proven stable and therefore can be administered as such.

In one embodiment, the present invention provides the use of EGF to treat or prevent enteric infections (viral, bacterial or parasitic) in an animal.

In another embodiment, the present invention provides the use of EGF to treat or prevent enteric colibacillosis (scours) in an animal.

In a further embodiment, the present invention provides the use of EGF to prevent gastric ulcers or to accelerate the healing of gastric ulcers associated with Helicobacter pylori.

In another aspect, the present invention provides the use of EGF to increase weight gain in an animal. This is useful in increasing production in the animal industry such as the agriculture industry and aquaculture industry where there is a demand for non-drug food additives that enhance production.

In a further aspect, the present invention the use of EGF to increase immunoglobulin absorption in the intestine of an animal, especially a newborn animal.

In yet a further aspect, the present invention provides the use of an agent that inhibits the activity of EGF to decrease intestinal absorption of nutrients. This may be useful in situations where decreased intestinal absorption is desired such as in treating obesity or in decreasing the intestinal absorption of toxins.

The present invention also includes within its scope the use of EGF to prepare a medicament to treat or prevent any of the conditions mentioned above.

DETAILED DESCRIPTION OF THE INVENTION

Example 1

Effect of EGF on Intestinal Infection

Figure 1:
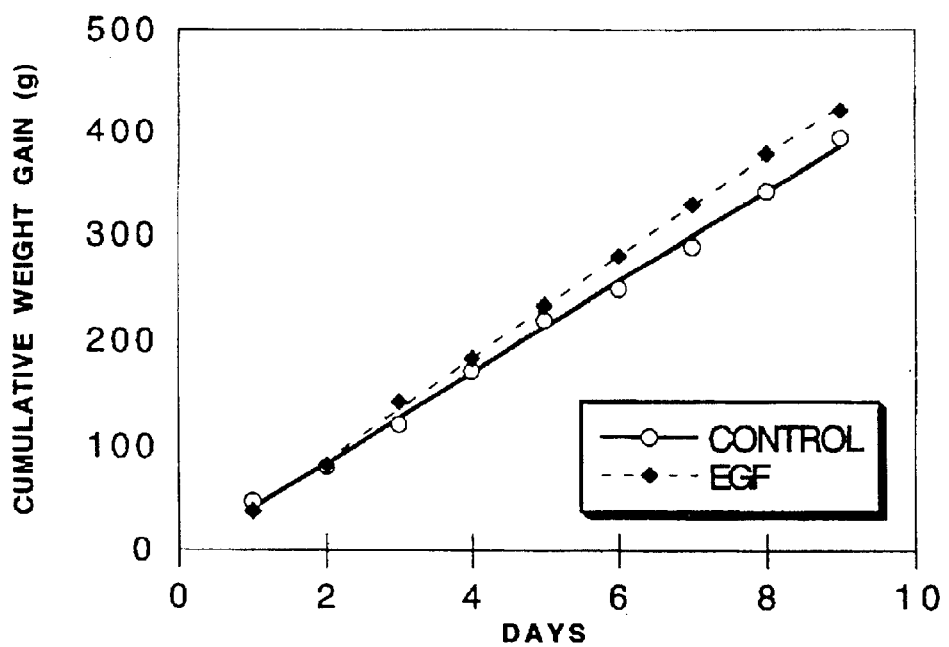
FIG. 1 is a graph showing the effect of EGF on weight gain in rabbits.

Experiments were conducted in order to determine the effects of EGF on intestinal infection by E. coli. The results of the experiments have been combined and are summarized below.

Twenty-eight New Zealand White rabbits (6 wk-old) were studied in 3 groups: 1) Controls (Con, n=9), 2) Infected with $1 \times 10^7$ RDEC-E. coli (I, n=10), and 3) Infected-treated with 60 µg oral EGF daily for 10 days, starting 3 days prior to infection (I-EGF, n=9). Animals were assessed daily for weight gain, rectal passage of E. coli, and presence of diarrhea. Seven days post-infection, animals were killed and mucosa obtained from the jejunum (JEJ), ileum (ILE), and proximal colon (PROX) for quantitation of E. coli, and from the jejunum for mucosal enzyme assays.

The results of the experiments are shown in Table 1. Stool cultures for infected (I) and infected and treated with EGF (I-EGF) but not Control rabbits were positive for E. coli. In the I group, 4 animals had diarrhea compared to none in the I-EGF or Control animals. Infection resulted in reduced weight gain (WG) which is prevented by EGF (see Table 1). EGF treatment also reduced E. coli colonization in the jejunum, ileum and proximal colon by >85% compared to I, and prevented the decrease in jejunum maltase and sucrase activities.

The above results demonstrate that administration of EGF has a number of clinical benefits in rabbits infected with E. coli, as illustrated by enhanced weight gain and absence of diarrhea when compared to untreated infected animals. EGF treatment is associated with increased disaccharidase activities and reduced bacterial colonization in the intestinal mucosa.

Example 2

Effect of EGF on Intestinal Infection and Bacterial Translocation

An experiment was conducted in order to assess the effects of exogenous EGF on bacterial translocation across the epithelium in vitro and to determine if the effects of EGF are bacteria-specific.

Two$\times 10^8$ human pathogenic Salmonella typhimurium or E. coli were added to the apical surface of confluent human CaCo2 monolayers grown on Transwell membranes (porosity 3.0 µm). Monolayers received apical EGF (100 µM) or PBS 15 min prior to infection. Each hour post infection (0–7 h), medium under the membrane was replaced and bacterial transepithelial migration rate (CFU/h) was calculated.

The results demonstrate that, in vitro, EGF delayed the initial E. coli translocation by 1 hour and inhibited the rate of invasion by >95% thereafter. Translocation of S. typhimurium was completely abolished in EGF-treated monolayers.

The above results demonstrate that EGF exerts its clinical benefits at least in part by interfering with bacterial translocation. EGF may also exert its effect in controlling bacterial colonization by interfering with bacterial multiplication and/or interfering with adherence of the bacterial to the intestinal surface. The latter was further suggested by scanning electron microscopy in the Transwell membrane studies. Indeed, these observations revealed significantly higher numbers of microorganisms adhering to the epithelial surface of untreated monolayers compared with those that had been exposed to EGF. The findings further support that EGF therapy may be useful in treating or preventing enteric infections.

Example 3

Effect of EGF on Weight Gain

EGF was tested for its potential benefits on weight gain. One group of New Zealand white rabbits (6 week old, 500–700 g) received daily oral doses of recombinant human EGF (100 µg/kg body weight) and control animals were given saline only. At 9 days, EGF-treated animals had a mean cumulative weight gain of 422±27 g (n=10) while controls only gained 394±16 g (n=11). Referring to FIG. 1, the slope of the linear regression curve of weight gain in EGF treated animals was significantly greater (P 0.002) than that of untreated controls. Given the linear aspect of both curves, continued feeding with EGF is likely to produce a steadily increasing. effect on weight gain.

These results indicate that EGF can promote the acceleration of weight gain in healthy animals.

Example 4

Effect of EGF and an EGF Receptor Inhibitor on Nutrient Absorption

These experiments were conducted to determine the effects of EGF and an EGF receptor inhibitor on nutrient absorption and brush border ultrastructure.

Initial experiments demonstrated that luminal EGF increased glucose absorption in intact tissue. Subsequent experiments examined the effects of EGF and an inhibitor of the EGF receptor (tyrphostin 51) on intestinal brush border membrane nutrient absorption. Tyrphostin 51is a specific inhibitor of tyrosine kinase, which is a critical element of the EGF intracellular signalling cascade. Studies were performed in New Zealand White rabbits (700–1000 g; approximately 8 weeks of age). Two 10 cm blind jejunal loops separated by a 1 cm segment were tied off starting 5 cm distal to the ligament of Treitz. In separate experiments either EGF (60 ng/ml), EGF+tyrphostin (10 $\mu$M), or tyrphostin (10 $\mu$M) alone in 1.5 ml of saline vehicle was administered to one of the loops. The other loop received vehicle alone and served as a paired control. After one hour, the loops were removed and the mucosa scraped for preparation of brush border membrane vesicles. Nutrient (D-glucose and L-proline) uptake into brush border membrane vesicles was determined by established techniques. Luminal EGF stimulated a significant increase ($p<0.001$) in brush border membrane glucose (EGF 16.1±1.0 vs CONTROL 11.5±0.9 nmol/min/mg protein; n=5) and proline (EGF 3.8±0.5 vs CONTROL 2.6±0.3 nmol/min/mg protein; n=5) transport compared to controls. Both glucose and proline transport were enhanced to a similar degree suggesting EGF stimulates a generalized increase in nutrient transport. Concurrent tyrphostin (TYR) administration completely blocked the EGF-induced increase in glucose uptake and resulted in a significant ($p<0.001$) reduction in nutrient uptake compared to controls (EGF+TYR 5.9±0.3 vs CONTROL 10.7±0.6 nmol/min/mg protein; n=4). Subsequently, a further series of experiments examined the effect of tyrphostin alone on brush border glucose transport. Tyrphostin alone significantly ($p<0.001$) reduced glucose uptake compared to controls (TYR 8.0±0.8 vs CONTROL 10.7±1.0 nmol/min/mg protein; n=4). The inventors have previously demonstrated the intestinal nutrient absorption correlates with weight gain in a number of different models. Thus, EGF treatment increases nutrient absorption and promotes weight gain. Conversely, tyrphostin treatment may promote a decrease in weight gain or weight loss and therefore may be useful in the treatment of obesity. Tyrphostin treatment may also reduce the intestinal uptake of toxic or adverse substances.

Example 5

Effect of EGF on Immunoglobulin Absorption

In another series of experiments, EGF was tested for its ability to enhance immunoglobulin uptake in the intestine of young animals.

Rats (14 day-old, Sprague-Dawley) were randomly allocated to one of 3 groups. At time 0, one of 3 solutions was delivered by oral lavage to each group: Group 1 was given saline only (0.4 mL); Group 2 received saline (0.2 mL)+ sheep IgG (0.2 mL, 5 mg/mL); Group 3 received EGF in saline (0.1 $\mu$g/mL)+sheep IgG (0.2 mL, 5 mg/mL). One, two and four hours post inoculation, blood was collected from 4 animals in each group by cardiac puncture (after anaesthesia with methoxyfluorane). The serum was separated, and levels of sheep IgG were determined by Enzyme-Linked Immunosorbant Assay (ELISA). Values were expressed as mean ± standard error serum sheep IgG ($\mu$g/mL) (Table 2).

The results are shown in Table 2 and indicate that administration of EGF increases the uptake of immunoglobulin from the intestine.

The above describes new utilities for EGF. In particular, EGF has been shown to prevent gastrointestinal colonization by pathogens and to promote weight gain in animals. Further, EGF may increase immunoglobulin absorption in young animals. Consequently, EGF is a very useful agent that can be used to increase production in the animal industry such as the beef, pig and poultry industry as well as in aquaculture. In addition, EGF treatment may have clinical benefits in humans (i.e. during Crohn's disease, gastrointestinal infection, traveller's diarrhea, etc.). EGF may also accelerate healing of gastrointestinal ulcers by preventing colonization at the ulcer site.

Inhibitors of EGF may decrease nutrient absorption in the intestine and as such may be useful in treating obesity or in preventing absorption of toxins.

One skilled in the art will appreciate that the present invention relates to new utilities of EGF and inhibitors of EGF. The examples described are meant to be models to exemplify the invention and not to limit the invention. The mode of administration, the formulation and the dose of the EGF or EGF inhibitor can be varied depending on the particular utility. For example, when treating young farm animals the EGF can be administered orally in the feed or drinking water of the animal. The dose range can be varied from 10–10,000 $\mu$g/kg per day.

TABLE 1

| | Cumulative Weight Gain | E. Coli ($Log_{10}$ CFU/cm) | | | MALT | SUC |
|---|---|---|---|---|---|---|
| | (grams) | JEJ | ILE | PROX | (u/g) | (u/g) |
| CONTROL | 314 ± 23 | 0 | 0 | 0 | 301 ± 106 | 77 ± 17 |
| INFECTED | 237 ± 27 | 4.19 ± 0.3 | 6.16 ± 0.3 | 4.92 ± 0.3 | 151 ± 36 | 28 ± 3 |
| INFECTED + EGF | 316 ± 16* | 3.10 ± 0.4* | 4.88 ± 0.2* | 4.09 ± 0.2* | 436 ± 48* | 89 ± 19* |
| % BACTERIAL CLEARANCE IN INFECTED + EGF GROUP | | 92% | 95% | 85% | | |

Values are means ± Standard error from mean of 5 animals per group 7 days after inoculation.
*$P < 0.05$ I-EGF vs. I.

TABLE 2

Concentration of sheep IgG (µg/mL) in the serum of rats.

| Time (Post-Inoculation) | Group 1 (Saline) | Group 2 (Saline + IgG) | Group 3 (EGF + IgG) |
|---|---|---|---|
| 1 hour | 0 ± 0 | 1.2 ± 0.8 | 4.7 ± 1.9 |
| 2 hours | N/A | 4.4 ± 1.5 | 9.8 ± 3.9 |
| 4 hours | 0 ± 0 | 5.8 ± 2.2 | 12.2 ± 3.8 |

N/A = not available

REFERENCES

1. Radostits O M, Blood D C, Gay C C (eds). Veterinary medicine. Baillere Tindall 8th Ed., London. 1994, pp 703–730.
2. Acres S D. Enterotoxigenic *E. coli* infections in newborn calves: a review. J. Dairy Sci. 1985:68;229–256.
3. Janke B H, Francis D H, Collins J E, et al. Attaching and effacing *E. coli* infection as a cause of diarrhea in young calves. JAVMA 1990;196(6):897–901.
4. Grimes S D, Waxler G L, Newman J P. Adhesion of K99-positive *E. coli* to intestinal brush borders of pigs. Am J Vet Res. 1986;47(2):385–388.
5. Bijlsm a I G W, deNijs A, van der Meer C, et al. Different pig phenotypes affect adherence of *E. coli* to jejunal brush borders by K88ab, K88ac, K88ad antigen. Infect Immun 1982;37:891–894.
6. Mainil J G, Bex F, Jacguemin E, et al. Prevalence of four enterotoxin (STaP,STaH,STb,and LT) and four adhesin subunit (K99, K88,987P, and F41) genes among *E. coli* isolates from cattle. Am J Vet Res. 1990;51(2) 187–190.
7. Schoonderwoerd M, Clarke R C, van Dreumal A A, et al. Colitis in calves: Natural and experimental infection with a verotoxin-producing strain of *E. coli* O111:NM. Can J Vet Res. 1988;52:484–487.
8. Hadad J J, Gyles C L. Scanning and transmission electron microscopic study of the small intestine of colostrum-fed calves infected with-selected strains of *E. coli*. Am J Vet Res. 1982;43(1) 41–49.
9. Elliott E, Li Z, Bell C, et al. Modulation of host response to *E. coli* O157:H7 infection by antiCD18 antibody in rabbits. Gastroenterology 1994;106:1554–1561.
10. Weaver L T, Gonella P A, Israel E J, et al. Uptake and transport of Epidermal Growth Factor by the small intestinal epithelium of the fetal rat. Gastroenterology 1990;98:828–837.
11. O'Loughlin E V, Chung M, Hollenberg M, et al. Effect of epidermal growth factor on ontogeny of the gastrointestinal tract. Am J Physiol 1985;249:G674-G678.
12. Goodlad R A, Raja K B, Peters T J, et al. Effects of urogastrone-epidermal growth factor on intestinal brush border enzymes and mitotic activity. Gut 1991;994–998.
13. Walker-Smith J A, Phillips A D, Walford N, et al. Intravenous epidermal growth factor/urogastrone increases small intestinal cell proliferation in congenital microvillous atrophy. Lancet 1985;ii:1239–1240.
14. Hardin J A, Buret A, Meddings J B, et al. Effect of epidermal growth factor on enterocyte brush-border surface area. Am J Physiol 1993;264:G3120G318.
15. O'Loughlin E V, Winter M, Shun A, et al. Structural and functional adaptation following jejunal resection in rabbits: Effect of epidermal growth factor. Gastroenterology 1994;107:87–93.
16. Pothier P, Menard D. Presence and characteristics of epidermal growth factor receptors in human fetal small intestine and colon. FEBS lett. 1988;228(1) 113–117.
17. Brake A J, Merryweather J P, Coit D G, et al. α-factor directed synthesis and secretion of mature foreign proteins in *Saccharomyces cerevisiae*. Proc Natl Acad Sci USA 1984;81:4642–4646.
18. Brown G L, Curtsinger L, Brightwell J R, et al. Enhancement of epidermal regeneration by biosynthetic epidermal growth factor. J Exp Med 1986;163:1319–1324.
19. Brown G L, Nanney L B, Griffen J, et al. Enhancement of wound healing by topical treatment with epidermal growth factor. New Engl J Med 1989;321:76–79.
20. Zijistra R T, Odle J, Hall W F, et al. Effect of orally administered epidermal growth factor in intestinal recovery of neonatal pigs infected with rotavirus. J Ped Gastro Nutr 1994;19:382–390.
21. Bird A R, Croom W J, Fan Y K, et al. Jejunal glucose absorption is enhanced by epidermal growth factor in mice. J Nutr 1994;124:231–240.
22. Hardin J A, Gall D G. The effect of TGFα on intestinal solute transport. Reg Pep 1992;39:169–176.
23. Horwath K, Hill I D, Devarajan P, et al. Short-term effect of epidermal growth factor on sodium and glucose cotransport of isolated jejunal epithelial cells. Biochem Biophys Acta Mol Cell Res 1994;1222:215–222.
24. Kitagawa T, Tanaka M, Akamatsu Y. Regulation of glucose transport activity and expression of glucose transporter mRNA by serum, growth factors, and phorbol ester in quiescent mouse fibroblasts. Biochem Biophys Acta 1989;980:100–108.
25. Opleta-Madsen K, Hardin J A, Gall D G. Epidermal growth factor upregulates intestinal electrolyte and nutrient transport. Am J Physiol 1991;260:G807-G814.
26. Opleta-Madsen K, Meddings J B, Gall D G. Epidermal growth factor and postnatal development of intestinal transport and membrane structure. Pediatr Res 1991;30:342–350.
27. Salloum R M, Stevens B R, Schultz G S, et al. Regulation of small intestinal glutamine transport by epidermal growth factor. Surgery 1993;113:552–559.
28. James P S, Smith M W, Tivey D R, et al. Dexamethasone selectively increases sodium-dependent alanine transport across neonatal piglet intestine. J Physiol 1987;393:569–582.
29. Jaeger L A, Lamar C H, Cline T R, et al. Effect of orally administered epidermal growth factor on the jejunal mucosa of weaned pigs. Am. J. Vet. Res. 1990;5(3):471–474.
30. Brown G L, Nanney L B, Griffin J, et al. Enhancement of wound healing by topical treatment with epidermal growth factor. New Engl. J. Med. 1989;321(2):76–79.
31. Aldridge B, Garry F, Adams R. Role of colostral tranfer in neonatal calf management: Failure of acquisition of passive immunity. Continuing education article #8. Compend. N. Am. Ed. 1992;14(2):265–269.
32. Donowitz M, Montgomery J L M, Walker M S, et al. Brush border tyrosine phosphorylation stimulates ileal neutral NaCl absorption and brush border $Na^+H^+$ exchange. Am J Physiol 1994;266:G647-G656.

What is claimed is:

1. A method to reduce bacterial colonization of gastric ulcer sites in an animal, comprising administering to said animal an amount of epidermal growth factor (EGF) effective to reduce bacterial colonization of gastric ulcer sites.

2. The method of claim 1 wherein said bacterial colonization is colonization by *Helicobacter pylori*.

3. The method of claim 1 wherein said administration accelerates healing of gastric ulcers.

4. The method of claim 1 wherein said administration is oral administration.

5. The method of claim 1 wherein said EGF is administered in the feed of said animal.

6. The method of claim 1 wherein said effective amount is from 10–10,000 µg/kg per day.

* * * * *